US009096508B2

(12) United States Patent
Kanaya et al.

(10) Patent No.: US 9,096,508 B2
(45) Date of Patent: Aug. 4, 2015

(54) METHOD FOR PRODUCING CAROTENOID COMPOSITION

(75) Inventors: Kento Kanaya, Takasago (JP); Koichi Kinoshita, Takasago (JP); Masaru Hirano, Takasago (JP)

(73) Assignee: KANEKA CORPORATION, Kita-ku (JP)

( * ) Notice: Subject to any disclaimer, the term of this patent is extended or adjusted under 35 U.S.C. 154(b) by 0 days.

(21) Appl. No.: 14/130,132

(22) PCT Filed: Jun. 29, 2012

(86) PCT No.: PCT/JP2012/066797
§ 371 (c)(1),
(2), (4) Date: Feb. 21, 2014

(87) PCT Pub. No.: WO2013/002398
PCT Pub. Date: Jan. 3, 2013

(65) Prior Publication Data
US 2014/0179657 A1    Jun. 26, 2014

(30) Foreign Application Priority Data
Jun. 30, 2011    (JP) ................................. 2011-146313

(51) Int. Cl.
*C12R 1/645*    (2006.01)
*C12P 23/00*    (2006.01)
(Continued)

(52) U.S. Cl.
CPC ............... *C07C 45/78* (2013.01); *A61K 31/122* (2013.01); *A61K 31/575* (2013.01); *A61K 36/07* (2013.01); *C07C 403/24* (2013.01); *C12P 23/00* (2013.01); *C07C 2101/14* (2013.01)

(58) Field of Classification Search
CPC .................................. C12R 1/645; C12P 23/00
USPC .......................................................... 568/824
See application file for complete search history.

(56) References Cited

U.S. PATENT DOCUMENTS 6,818,239 B2 *  11/2004  Kagan et al. .................. 426/429
2003/0044495 A1   3/2003  Kagan et al.
(Continued)

FOREIGN PATENT DOCUMENTS

EP    2 017 262 A1    1/2009
JP    7-101827 A      4/1995
(Continued)

OTHER PUBLICATIONS

International Preliminary Report on Patentability and Written Opinion issued Aug. 14, 2012 in PCT/JP2012/066797 (English Translation only).

(Continued)

*Primary Examiner* — Kamal Saeed
*Assistant Examiner* — Janet L Coppins
(74) *Attorney, Agent, or Firm* — Oblon, McClelland, Maier & Neustadt, L.L.P.

(57) ABSTRACT

The present invention provides an efficient method for industrially producing a naturally-derived carotenoid composition with a large amount of a carotenoid such as astaxanthin from a culture of a yeast of the genus *Xanthophyllomyces* without requiring any special extraction equipment and any complicated refinement process and without any need for organic solvents harmful to humans. Provided is a method for producing a carotenoid composition, including the steps of washing a carotenoid-containing yeast of the genus *Xanthophyllomyces* with an organic solvent (A) at 30° C. or lower, and extracting a carotenoid from the washed yeast with an organic solvent (B) at 10° C. to 70° C.

15 Claims, 1 Drawing Sheet (51) Int. Cl.
  *C07C 45/78* (2006.01)
  *C07C 403/24* (2006.01)
  *A61K 31/122* (2006.01)
  *A61K 31/575* (2006.01)
  *A61K 36/07* (2006.01)

(56) References Cited

U.S. PATENT DOCUMENTS

| | | |
|---|---|---|
| 2003/0087335 A1 | 5/2003 | Han et al. |
| 2005/0059134 A1 | 3/2005 | Schaap et al. |
| 2009/0130730 A1 | 5/2009 | Abe et al. |
| 2010/0174118 A1 | 7/2010 | Ishizaki et al. |
| 2010/0291251 A1 | 11/2010 | Takahashi et al. |
| 2012/0202889 A1 | 8/2012 | Inoue et al. |

FOREIGN PATENT DOCUMENTS

| | | | |
|---|---|---|---|
| JP | 10-276721 A | 10/1998 | |
| JP | 11-56346 A | 3/1999 | |
| JP | 2004-41147 A | 2/2004 | |
| JP | 2004-208504 A | 7/2004 | |
| JP | 2007 319015 | 12/2007 | |
| WO | WO 01/55100 A1 | 8/2001 | |
| WO | WO 01/83437 A1 | 11/2001 | |
| WO | WO 2007/020057 A1 | 2/2007 | |
| WO | 2009/028643 * | 3/2009 | ............. C12P 23/00 |
| WO | 2009 028643 | 3/2009 | |
| WO | 2011 018896 | 2/2011 | |
| WO | WO 2011/018896 A1 | 2/2011 | |

OTHER PUBLICATIONS

International Search Report Issued Aug. 14, 2012 in PCT/JP12/066797 Filed Jun. 29, 2012.

* cited by examiner

METHOD FOR PRODUCING CAROTENOID COMPOSITION

TECHNICAL FIELD

The present invention relates to a method for producing a carotenoid composition. More specifically, the present invention relates to a method for producing a carotenoid composition, the method including extracting a carotenoid such as astaxanthin from a yeast of the genus *Xanthophyllomyces*.

BACKGROUND ART

Carotenoids are known as natural pigments with colors ranging from yellow through orange to red or purple, widely found in nature. Astaxanthin, one of carotenoids, is widely used in feeds for enhancing the color of fish and chicken eggs. Astaxanthin is also approved as a food additive and widely used in fat processed foods, protein foods, aqueous liquid foods, health foods, and the like. Moreover, since astaxanthin has strong antioxidant effects such as antioxidative activity against free radical-induced lipid peroxidation, and singlet oxygen scavenging activity which is several hundred times more powerful than that of α-tocopherol, nowadays astaxanthin is expected to be used in cosmetics, functional foods and drugs so that its antioxidant effects may prevent the generation of excessive active oxygen in the body, for example, to improve skin blemishes and wrinkles; to prevent cataract, arteriosclerosis, and heart disease; to enhance immunity; and to prevent cancer.

Astaxanthin is widely found in nature, for example, in fishes such as salmons, trouts, and red sea breams; and crustaceans such as crabs, shrimps, and krills. Also, astaxanthin is produced by microorganisms such as bacteria belonging to the genus *Paracoccus*, the genus *Brevibacterium*, and the like; algae such as *Hematococcus pluvialis*; and yeasts such as *Xanthophyllomyces dendrorhous* (also known as *Phaffia rhodozyma*). Carotenoids such as astaxanthin and zeaxanthin currently widely used are provided by chemical synthesis in terms of stable supply and costs. However, chemically synthesized carotenoids have the risk of contamination of process-related contaminants and particularly poisons that are used in synthesis reactions and harmful to humans. Thus, supplying naturally-derived products is desired in terms of safety.

With such a background, many reports have been published to disclose methods for producing carotenoids including astaxanthin using natural algae and microorganisms that are considered to be suitable for industrial mass production. For example, a method using *Haematococcus* algae is reported in which cultured cyst cells of algae are treated with hot acetone to elute chlorophyll that is a contaminant, and then astaxanthin is extracted with ethanol (Patent Literature 1). The carotenoid composition obtained by this method, however, contains many biological contaminants. Thus, this method has difficulty in industrially producing a carotenoid composition with a sufficient amount of astaxanthin. In addition, it is difficult for this method to remove the acetone used in the production to reduce it to, for example, a level equal to or less than the amount specified in food additive regulations.

Another report (Patent Literature 2) discloses a method for producing a composition containing 0.5 to 60% of astaxanthin without using organic solvents harmful to humans. This method includes kneading *Haematococcus* algae with broken cell walls with a cosolvent such as water or glycerin to give a formed body, filling an extraction tank with the formed body, and supplying supercritical fluid thereto to extract astaxanthin. However, for example, mass production by this method needs special equipment and also requires a long period of time for extraction to achieve a sufficient yield. Besides, the composition obtained by this method needs additional concentration for achieving a high astaxanthin content. Thus, this method cannot satisfy simplicity and cost efficiency for industrial production of a highly-concentrated carotenoid composition.

A method using a yeast of the genus *Xanthophyllomyces* (the genus *Phaffia*) is also reported in which the yeast cells are subjected to extraction in an n-hexane-ethanol mixed solvent while they are crushed with a compression crusher; the extract is concentrated to give an oily substance; the oily substance cooled at −50° C. is suspended and then filtered to remove free fatty acids and triglycerides; and residual free fatty acids in the pigment oil are further removed through conversion to metal soaps, whereby a high concentration of astaxanthin can be obtained (Patent Literature 3). Still another report (Patent Literature 4) discloses a method including extracting disrupted cells of the genus *Xanthophyllomyces* (the genus *Phaffia*) with an organic solvent, concentrating the extract to give an oily crude extract, and refining the crude extract by a refining method such as ion-exchange chromatography or adsorption chromatography to obtain astaxanthin or an ester thereof. These methods, however, include complicated processes. In particular, the latter method includes a troublesome step of refining a low-concentration crude astaxanthin solution by multiple column chromatography operations. Thus, industrial production by these methods is difficult.

Meanwhile, other reports (Patent Literatures 5 and 6) disclose preparation of dry products containing 40% or more of astaxanthin by extracting a novel bacterium (E-396 strain) capable of producing astaxanthin, with a lower alcohol or a mixture of a lower alcohol and water, concentrating the extract to give a precipitate, and washing the precipitate with lower alcohols. These methods enable preparation of a highly-concentrated astaxanthin composition only using water and a highly safe solvent such as ethanol. In the method of Patent Literature 5 including extraction at 80° C. or higher, however, the extraction needs to be performed in a sealable pressure vessel and such a high-temperature operation may convert part of naturally-derived free trans-astaxanthin to the cis form, which unfortunately may reduce the refining yield of astaxanthin having the desired structure. Moreover, the methods of Patent Literatures 5 and 6 are unclear if they are applicable to species other than the novel bacterium that has been actually confirmed to enable the preparation of such astaxanthin compositions.

Still another report (Patent Literature 7) discloses a production method that includes extracting cultured yeast cells of the genus *Xanthophyllomyces* (the genus *Phaffia*) with acetone, concentrating the extract to give a crude extract, and adding a hydrocarbon solvent to the crude extract to cause crystallization. This method has some advantages such as high simplicity and capability of obtaining a composition with a high astaxanthin content of 40% or higher. However, this method, which uses a hydrocarbon solvent in the production, may allow this solvent to remain in the resulting composition.

In particular, yeasts of the genus *Xanthophyllomyces* are known to contain about 25% by weight of lipids per dry cell weight, and extracts from these yeasts mainly contain lipids. Thus, concentrating such an extract results in a sticky, viscous concentrate. For this reason, when a composition with a high concentration of astaxanthin is prepared using a yeast of the genus *Xanthophyllomyces*, many kinds of contaminants such as lipids need to be removed during the preparation process. Accordingly, this requires a complicated and non-industrial process or an organic solvent such as hexane which is harmful to humans and the residual amount of which in final products should meet regulations.

In such circumstances, desired is a simple method for producing a naturally-derived carotenoid composition having a high astaxanthin content but a low residual solvent content or a residual solvent content that causes no problem.

CITATION LIST

Patent Literature

Patent Literature 1: JP H11-56346 A
Patent Literature 2: JP 2004-41147 A
Patent Literature 3: JP H07-101827 A
Patent Literature 4: JP H10-276721 A
Patent Literature 5: WO 2009/028643
Patent Literature 6: JP 2007-319015 A
Patent Literature 7: JP 2004-208504 A

SUMMARY OF INVENTION

Technical Problem

As mentioned above, conventional methods for producing naturally-derived carotenoid compositions with a high astaxanthin content require special equipment for extraction or complicated and non-industrial processes for removing contaminants such as lipids derived from cells, for example. Thus, unfortunately, these methods cause troublesome operations and cost increase. Furthermore, methods using an organic solvent unsuitable for eating, such as hydrocarbon solvents, in the production have a problem in removing the residual solvent. In particular, in the case of using a yeast of the genus *Xanthophyllomyces* with a high lipid content, refinement for obtaining a high concentration of astaxanthin is difficult, or even if possible, is a quite complicated process. Especially, powdering an astaxanthin-containing composition on an industrial scale was considered virtually impossible. The present inventors applied a yeast of the genus *Xanthophyllomyces* to the method of Patent Literature 5, for example, and found that the resulting precipitate contained a large amount of lipids, which precluded operations such as filtering in the washing step and thus made it difficult to provide a production with sufficient efficiency.

The present invention aims to provide an efficient method for industrially producing a naturally-derived carotenoid composition with a high concentration of a carotenoid such as astaxanthin from a culture of a yeast of the genus *Xanthophyllomyces* without requiring any special extraction equipment and any complicated refinement process and without any need for organic solvents harmful to humans.

Solution to Problem

The present inventors conducted intensive studies to solve the above problems and found that a method including washing a yeast of the genus *Xanthophyllomyces* under specific conditions before extracting a carotenoid from the yeast enables to efficiently extract a carotenoid such as astaxanthin from a yeast of the genus *Xanthophyllomyces*, and that this method is suitable for industrial production, thereby completed the present invention.

Specifically, the present invention relates to a method for producing a carotenoid composition, including the steps of washing a carotenoid-containing yeast of the genus *Xanthophyllomyces* with an organic solvent (A) at 30° C. or lower, and extracting a carotenoid from the washed yeast with an organic solvent (B) at 10° C. to 70° C.

The carotenoid is preferably astaxanthin.

The organic solvent (A) is preferably at least one selected from the group consisting of ketones, alcohols, hydrocarbons, ethers, and fatty acid esters.

The organic solvent (B) is preferably at least one selected from the group consisting of alcohols, hydrocarbons, and ethers.

The organic solvent (A) and the organic solvent (B) are preferably both ethanol.

The method preferably further includes the step of concentrating the resulting carotenoid extract to form an oily composition.

The oily composition preferably has an astaxanthin content of 1 to 20% by weight.

The method preferably further includes the step of precipitating the carotenoid from the resulting carotenoid extract and subjecting the resulting precipitate to solid-liquid separation to form a powdered composition.

The powdered composition preferably has an astaxanthin content of 20 to 80% by weight.

The present invention also relates to a carotenoid composition, containing astaxanthin that has a powder X-ray diffraction pattern including peaks at diffraction angles of 13.3° (2θ±0.2°), 13.8° (2θ±0.2°), 14.3° (2θ±0.2°), 15.8° (2θ±0.2°), 16.3° (2θ±0.2°), 18.2° (2θ±0.2°), 20.5° (2θ±0.2°), 24.8° (2θ±0.2°), and 25.3° (2θ±0.2°), and has a chemical structure of (3R, 3'R).

The carotenoid composition is preferably in a powder form with a Dr. Carr's flowability index of 60 or higher.

The carotenoid composition preferably has an astaxanthin content of 20 to 80% by weight.

Moreover, the present invention relates to a carotenoid composition, which is an oily composition including astaxanthin derived from a yeast of the genus *Xanthophyllomyces*, wherein the composition has a ratio of ergosterol content to astaxanthin content of 40% by weight or lower.

The carotenoid composition preferably has an astaxanthin content of 1 to 20% by weight and a viscosity at a temperature of 30° C. and a shear rate of 100 s$^{-1}$ of 0.01 to 1 Pa·s.

Advantageous Effects of Invention

In the production method of the present invention, most of contaminants such as lipids in a yeast of the genus *Xanthophyllomyces* are removed in advance, which makes it possible to efficiently perform the subsequent extraction and concentration of a carotenoid. Thus, the present invention provides a method for producing a naturally-derived carotenoid composition, which is simple and suitable for industrial production. The production method of the present invention can be performed only using safe and edible solvents, and thus enables a simple production with a low residual solvent content or a residual solvent content that causes no problem.

The carotenoid composition produced according to the present invention can be provided in a powder form with excellent powder flowability as well as containing a high concentration of a target carotenoid such as astaxanthin. Moreover, when the carotenoid composition produced according to the present invention is mixed with an edible liquid oil or fat to form an oily composition, the oily composition can have a lower viscosity and better handleability than prior art oily compositions with the same astaxanthin content as the former composition.

DESCRIPTION OF EMBODIMENTS

The following describes embodiments of the present invention in detail.

The present invention provides a method for producing a carotenoid composition, including the steps of washing a carotenoid-containing yeast of the genus *Xanthophyllomyces* with an organic solvent (A) at 30° C. or lower, and extracting a carotenoid from the washed yeast with an organic solvent (B) at 10° C. to 70° C.

The carotenoid in the present invention is not particularly limited, and specific examples include carotenes such as α-carotene, β-carotene, γ-carotene, δ-carotene, and lycopene; and xanthophylls such as lutein, zeaxanthin, canthaxanthin, fucoxanthin, astaxanthin, and antheraxanthin. The production method of the present invention is particularly suitable for obtaining astaxanthin among these carotenoids. The astaxanthin obtained in the present invention may be a mixture of astaxanthin with other carotenoid(s).

The yeast of the genus *Xanthophyllomyces*, used as a material in the production method of the present invention, is not particularly limited as long as it produces a carotenoid. In particular, specific examples of the yeast of the genus *Xanthophyllomyces* producing astaxanthin as a carotenoid include *Xanthophyllomyces dendrorhous* (also known as *Phaffia rhodozyma*).

In the present invention, suitable examples include, in addition to wild type yeast strains of the genus *Xanthophyllomyces* as mentioned above, variants and recombinants of the yeasts of the genus *Xanthophyllomyces*, which are obtained by modification or improvement of transcriptional or translational activity of a gene related to biosynthesis of a target carotenoid, or of enzyme activity of its expressed protein.

The method for culturing the yeast of the genus *Xanthophyllomyces* used in the present invention is not particularly limited and may appropriately be a method suitable for the target yeast of the genus *Xanthophyllomyces* or for the production of a target carotenoid. Examples of carbon sources that may be used for culturing include, but are not limited to, sucrose, glucose, xylose, maltose, corn syrup, molasses, starch, glycerin, ethanol, acetic acid, lactic acid, citric acid, and succinic acid. These carbon sources may be used alone, or two or more thereof may be used in combination to increase the carotenoid content in cells. If two or more of carbon sources are used in combination, the carbon sources may be simultaneously added to a medium, or carbon source(s) may be replaced with different carbon source(s) in the middle of culturing. Examples of the latter case include culturing using, as carbon sources, glucose in the first half of culturing and xylose in the second half; culturing with glucose in the first half and maltose in the second half; culturing with glucose in the first half and ethanol in the second half; culturing with glucose in the first half and glycerin in the second half; and culturing with glucose in the first half and citric acid in the second half. The combinations are not limited to these, and any combinations of carbon sources may also be used.

Examples of nitrogen sources that may be used for culturing include, but are not limited to, ammonia, ammonium salts, urea, amino acids, yeast extract, peptone, and corn steep liquor. These nitrogen sources may be used alone, or two or more thereof may be used in combination as mentioned for the carbon sources. Examples of nutrients other than carbon sources and nitrogen sources include, but are not limited to, phosphorus sources such as phosphoric acid; minerals such as magnesium, potassium, sodium, copper, iron, zinc, manganese, and molybdenum; and vitamins such as biotin. These carbon sources, nitrogen sources, and other nutrients may be supplied at once, in portions, or continuously, for example. The culturing temperature is not particularly limited and is preferably 15° C. to 26° C. The pH of the culture fluid is not particularly limited and is preferably 3 to 7.

In the production method of the present invention, a carotenoid may be directly extracted from cells of a carotenoid-containing yeast of the genus *Xanthophyllomyces* cultured under the conditions mentioned above, or may optionally be extracted from homogenized cells obtained by homogenizing the yeast of the genus *Xanthophyllomyces*. Thus, the "yeast of the genus *Xanthophyllomyces*" in the production method of the present invention encompasses intact yeast cells themselves; dry cells prepared by freeze drying, spray drying, or the like; and cells subjected to cell homogenization described below. The homogenization of the yeast cells particularly contributes to efficient extraction of a carotenoid produced and accumulated in the yeast of the genus *Xanthophyllomyces*. Though cell homogenization is not always needed, the recovery efficiency of the carotenoid produced and accumulated in the cells will be reduced if the cells are not homogenized. In the homogenization of the yeast cells in the present invention, the cells are only required to be disrupted so that their surface structures such as cell walls are damaged to the extent that the target carotenoid can be extracted. Thus, complete disruption of the cell walls or fragmentation of the yeast cells is not always needed.

The form of the yeast of the genus *Xanthophyllomyces*, which is subjected to the aforementioned cell homogenization and/or washing with an organic solvent (A) mentioned later, may be any of the following: a culture fluid containing the yeast; a concentrate of the culture fluid; wet cells of the yeast of the genus *Xanthophyllomyces* obtained from the culture fluid by a common method such as pressure filtration, vacuum filtration, natural filtration, centrifugation, or decantation; washed wet cells; wet cells suspended in a solvent (such as water, physiological saline, buffer solutions); dry cells obtained by drying the wet cells or by drying the culture fluid containing the yeast by spray drying, freeze drying, or the like; the dry cells suspended in a solvent (such as water, physiological saline, and buffer solutions); and the like. The filtration may use a filter aid for efficient operation. If a filter aid is used, the resulting residue may be used as wet cells or dry cells in a subsequent operation without removing the used filter aid. In cell homogenization, a preferred form is an aqueous suspension in which the yeast of the genus *Xanthophyllomyces* is suspended in an aqueous solvent. From the viewpoint of operability and the like, more preferred as the aqueous suspension of the yeast of the genus *Xanthophyllomyces* are a culture fluid itself containing the yeast of the genus *Xanthophyllomyces*; a concentrate of the culture fluid; and a suspension of wet cells of the genus *Xanthophyllomyces* in a solvent.

The yeast of the genus *Xanthophyllomyces* may be homogenized by one of the methods below or by some of them in any order. Examples of the homogenization method include physical treatment, chemical treatment, enzymatic treatment, heat treatment, self-digestion, osmotic lysis, and plasmolysis.

Examples of the physical treatment include use of an apparatus such as a high-pressure homogenizer, a rotating blade homogenizer, an ultrasonic homogenizer, a French press, and a ball mill, and combinations of these.

Examples of the chemical treatment include a treatment using an acid (preferably a strong acid) such as hydrochloric acid and sulfuric acid; a treatment using a base (preferably a strong base) such as sodium hydroxide and potassium hydroxide; and combinations of these.

Examples of the enzymatic treatment include use of an enzyme such as lysozyme, zymolyase, glucanase, novozyme, protease, and cellulase, which may appropriately be combined.

The heat treatment may be performed, for example, at 60° C. to 140° C. for 30 minutes to 3 hours.

The self-digestion may be performed, for example, in the presence of a solvent such as ethyl acetate, or by heating at 30° C. to 60° C. for 1 to 48 hours.

In addition, a treatment with a solution that has a different salt concentration from the cells may cause osmotic lysis or plasmolysis of the cells. This method alone, however, often fails to achieve a sufficient cell homogenization effect and thus this method is preferably used in combination with another method such as the aforementioned physical treatment, chemical treatment, enzymatic treatment, heat treatment, or self-digestion. Among the homogenization methods, preferred are physical treatment, chemical treatment (particularly acid treatment, preferably using a strong acid (e.g. an acid having a pKa in an aqueous solution of 2.5 or lower)), and heat treatment. In terms of homogenization efficiency, more preferred are physical treatment and chemical treatment.

In the production method of the present invention, the carotenoid-containing yeast of the genus *Xanthophyllomyces* prepared as above is washed with an organic solvent (A) at 30° C. or lower. The washing is preferably performed on wet cells, dry cells or an aqueous suspension of the carotenoid-containing yeast of the genus *Xanthophyllomyces*. The water contents of the wet cells and dry cells and the cell concentration of the aqueous suspension are not particularly limited. Preferably, the water content is typically 20 to 75% by weight in the case of the wet cells, and typically 0.01 to 20% by weight in the case of the dry cells. The cell concentration of the aqueous suspension is typically 1 to 25% by dry weight.

The organic solvent (A) used for washing in the production method of the present invention is not particularly limited, and is preferably a solvent that does not dissolve a target carotenoid very much in the washing conditions. Preferred examples of such organic solvents include ketones, alcohols, hydrocarbons, ethers, and fatty acid esters.

The ketones are not particularly limited and suitably have 3 to 6 carbon atoms. Specific examples include acetone, methyl ethyl ketone, methyl butyl ketone, and methyl isobutyl ketone. Preferred are acetone and methyl ethyl ketone, and most preferred is acetone.

The alcohols are not particularly limited, and may be cyclic or acyclic, saturated or unsaturated alcohols. In general, saturated alcohols are preferred. The number of carbon atoms of the alcohol is typically 1 to 20, preferably 1 to 12, and more preferably 1 to 6. Particularly preferred are monovalent alcohols having 1 to 5 carbon atoms, divalent alcohols having 2 to 5 carbon atoms, and trivalent alcohols having 3 carbon atoms.

Specific examples of these alcohols include monovalent alcohols such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, and 4-methylcyclohexanol; divalent alcohols such as 1,2-ethanediol, 1,2-propanediol, 1,3-propanediol, 1,2-butanediol, 1,3-butanediol, 1,4-butanediol, 2,3-butanediol, and 1,5-pentanediol; and trivalent alcohols such as glycerin.

Preferred monovalent alcohols include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol, and 4-methylcyclohexanol. More preferred examples include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, and cyclohexanol. Still more preferred examples include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, and neopentyl alcohol. Particularly preferred examples include methanol, ethanol, 1-propanol, 2-propanol, 1-butanol, 2-butanol, isobutyl alcohol, 2-methyl-1-butanol, and isopentyl alcohol, and most preferred example is ethanol.

Preferred divalent alcohols include 1,2-ethanediol, 1,2-propanediol, and 1,3-propanediol, and most preferred is 1,2-ethanediol. The trivalent alcohol is preferably glycerin.

The hydrocarbons are not particularly limited and examples thereof include aliphatic hydrocarbons, aromatic hydrocarbons, and halogenated hydrocarbons. Preferred among these are aliphatic hydrocarbons and aromatic hydrocarbons, and more preferred are aliphatic hydrocarbons.

The aliphatic hydrocarbons are not particularly limited, and may be cyclic or acyclic, saturated or unsaturated aliphatic hydrocarbons. In general, saturated aliphatic hydrocarbons are preferred. The aliphatic hydrocarbon typically has 3 to 20 carbon atoms, preferably 5 to 12 carbon atoms, and more preferably 5 to 8 carbon atoms. Specific examples include propane, butane, isobutane, pentane, 2-methylbutane, hexane, 2-methylpentane, 2,2-dimethylbutane, 2,3-dimethylbutane, heptane, isomers of heptane (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, and cyclohexene. Preferred examples include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, and p-menthane. More preferred examples include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, and ethylcyclohexane. Still more preferred examples include pentane, hexane, cyclohexane, and methylcyclohexane. Particularly preferred are heptane and methylcyclohexane, and most preferred is heptane, in terms of providing a particularly high oxidation-preventing effect.

The aromatic hydrocarbons are not particularly limited. The aromatic hydrocarbon typically has 6 to 20 carbon atoms, preferably 6 to 12 carbon atoms, and more preferably 7 to 10 carbon atoms. Specific examples include benzene, toluene, xylenes, o-xylene, m-xylene and p-xylene, ethylbenzene, cumene, mesitylene, tetralin, butylbenzene, p-cymene, cyclohexylbenzene, diethylbenzene, pentylbenzene, dipentylbenzene, dodecylbenzene, and styrene. Preferred examples include toluene, xylenes, o-xylene, m-xylene, and p-xylene, ethylbenzene, cumene, mesitylene, tetralin, butylbenzene, p-cymene, cyclohexylbenzene, diethylbenzene, and pentylbenzene. More preferred examples include toluene, xylenes, o-xylene, m-xylene, and p-xylene, cumene, and tetralin. Most preferred is cumene.

The halogenated hydrocarbons are not particularly limited, and may be cyclic or acyclic, saturated or unsaturated halogenated hydrocarbons. In general, acyclic halogenated hydrocarbons are preferred. More preferred are chlorinated hydrocarbons and fluorinated hydrocarbons, and still more preferred are chlorinated hydrocarbons. The halogenated hydrocarbon suitably has 1 to 6 carbon atoms, preferably 1 to 4 carbon atoms, and more preferably 1 to 2 carbon atoms. Specific examples include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, and 1,1,1,2-tetrafluoroethane. Preferred examples include dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, and 1,1,1,2-tetrafluoroethane. More preferred examples include dichloromethane, chloroform, 1,2-dichloroethylene, trichloroethylene, chlorobenzene, and 1,1,1,2-tetrafluoroethane.

The ethers are not particularly limited, and may be cyclic or acyclic, saturated or unsaturated ethers. In general, saturated ethers are preferred. The ether typically has 3 to 20 carbon atoms, preferably 4 to 12 carbon atoms, and more preferably 4 to 8 carbon atoms. Specific examples include diethyl ether, methyl tert-butyl ether, dipropyl ether, diisopropyl ether, dibutyl ether, dihexyl ether, ethyl vinyl ether, butyl vinyl ether, anisole, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol monobutyl ether. Preferred examples include diethyl ether, methyl tert-butyl ether, dipropyl ether, diisopropyl ether, dibutyl ether, dihexyl ether, anisole, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, and ethylene glycol monoethyl ether. More preferred examples include diethyl ether, methyl tert-butyl ether, anisole, dioxane, tetrahydrofuran, ethylene glycol monomethyl ether, and ethylene glycol monoethyl ether. Still more preferred examples include diethyl ether, methyl tert-butyl ether, and anisole. Most preferred is methyl tert-butyl ether.

The fatty acid esters are not particularly limited, and examples thereof include propionic acid esters, acetic acid esters, and formic acid esters. Preferred are acetic acid esters and formic acid esters, and more preferred are acetic acid esters. The ester radicals are not particularly limited, and alkyl esters having 1 to 8 carbon atoms and aralkyl esters having 7 to 12 carbon atoms may be typically used, with alkyl esters having 1 to 6 carbon atoms being preferred, and alkyl esters having 1 to 4 carbon atoms being more preferred.

Specific examples of propionic acid esters include methyl propionate, ethyl propionate, butyl propionate, and isopentyl propionate. Preferred examples include ethyl propionate.

Specific examples of acetic acid esters include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Preferred examples include methyl acetate, ethyl acetate, propyl acetate, isopropyl acetate, butyl acetate, isobutyl acetate, sec-butyl acetate, pentyl acetate, isopentyl acetate, sec-hexyl acetate, and cyclohexyl acetate. More preferred examples include methyl acetate, ethyl acetate, propyl acetate, isopropyl acetate, butyl acetate, and isobutyl acetate. Most preferred is ethyl acetate.

Specific examples of formic acid esters include methyl formate, ethyl formate, propyl formate, isopropyl formate, butyl formate, isobutyl formate, sec-butyl formate, and pentyl formate. Preferred examples include methyl formate, ethyl formate, propyl formate, butyl formate, isobutyl formate, and pentyl formate. Most preferred is ethyl formate.

As the organic solvent (A) in the present invention, the solvents mentioned above may, of course, be used alone, or two or more of these may be used in combination. The solvents may be mixed with water before use. That is, the organic solvent (A) in the present invention encompasses water-containing organic solvents.

In the production method of the present invention, the temperature condition for washing is not particularly limited as long as the organic solvent (A) used in washing is at a temperature of 30° C. or lower, more preferably 20° C. or lower, still more preferably 10° C. or lower, and particularly preferably 8° C. or lower. The organic solvent (A) exceeding 30° C. increases the carotenoid content in the washing solution, and thereby reduces the amount of carotenoid extractable from the yeast, unfortunately resulting in a poor yield of carotenoid.

The amount of the organic solvent (A) used for washing varies depending on the kind of the organic solvent (A) used, the temperature for washing, and the target kind of carotenoid, and thus is not particularly limited. The amount of carotenoid lost in washing can be limited to some extent by, for example, setting a condition such that the solubility of the carotenoid in the organic solvent (A) is 30% by weight or lower, and specifically, by setting the amount of the organic solvent (A) per part by dry weight of cells to 200 parts by weight or less, more preferably 50 parts by weight or less, and still more preferably 20 parts by weight or less. However, in cases where the temperature of the organic solvent (A) in washing is considerably low, or where an organic solvent (A) hardly dissolving a target carotenoid (e.g. glycerin, hexane, ethyl acetate, toluene) is used, the same goal can be achieved even with a larger amount of the organic solvent (A) for washing.

In particular, when astaxanthin is targeted as the carotenoid to be obtained, the organic solvent (A) is preferably a ketone or an alcohol, more preferably acetone or ethanol, and still more preferably ethanol. If acetone or ethanol is used as the organic solvent (A), for example, the amount thereof per part by dry weight of cells is not particularly limited, and is, for example, preferably 0.1 parts by weight or more, more preferably 1 part by weight or more, and still more preferably 5 parts by weight or more, whereas it is preferably 200 parts by weight or less, more preferably 50 parts by weight or less, and still more preferably 20 parts by weight or less.

In the production method of the present invention, the method for washing the carotenoid-containing yeast of the genus *Xanthophyllomyces* with the organic solvent (A) is not particularly limited, and examples thereof include a method including mixing with an impeller, a static mixer, a pump or the like; and a method of adding the organic solvent (A) to the yeast of the genus *Xanthophyllomyces* on a filtration plate during filtration of the cells, whereby washing by filtration is performed. In terms of washing efficiency, preferred is a washing method that includes contacting and mixing the organic solvent (A) with the carotenoid-containing yeast of the genus *Xanthophyllomyces* using an impeller for a certain period of time, and then separating the yeast of the genus *Phaffia* from the organic solvent (A). In this case, the time for washing (i.e., the time for contacting the organic solvent (A) with the carotenoid-containing yeast of the genus *Xanthophyllomyces*) is not particularly limited, and is preferably 24 hours or less, more preferably 1 minute to 6 hours, and still more preferably 10 minutes to 3 hours. Appropriate adjustment of the time for washing can limit the amount of carotenoid lost in washing to some extent. The method for separating the yeast of the genus *Xanthophyllomyces* from the organic solvent (A) after washing is not particularly limited, and a typical method such as pressure filtration, vacuum filtration, natural filtration, centrifugation, or decantation may be employed. These methods may, of course, be used in combination. In the filtration, a filter aid may be used for efficiency.

In the production method of the present invention, the yeast of the genus *Xanthophyllomyces* is previously washed with the organic solvent (A) before extraction as mentioned above. This removes most of the contaminants such as lipids derived from the yeast cells of the genus *Xanthophyllomyces* which contain a large amount of lipids, so as to increase the concentration in the target carotenoid composition as a final product, reduce the viscosity thereof in the form of an oily composition, and improve powder flowability thereof in the form of a powdered composition. Also, in the production process, this operation can, for example, reduce stickiness of the resulting composition caused by residual lipids to greatly improve problems such as attachment within an apparatus, and thus can improve production efficiency and productivity.

In the production method of the present invention, a target carotenoid is then extracted with an organic solvent (B) at 10° C. to 70° C. from the yeast of the genus *Xanthophyllomyces* washed with the organic solvent (A).

The organic solvent (B) used for extraction in the production method of the present invention is not particularly limited as long as it is capable of efficiently extracting a target carotenoid, and preferred examples thereof include alcohols, hydrocarbons, and ethers.

The alcohols are not particularly limited, and may be cyclic or acyclic, saturated or unsaturated alcohols. In general, saturated alcohols are preferred. The number of carbon atoms of the alcohol is typically 1 to 20, preferably 1 to 12, and more preferably 1 to 6. Particularly preferred are monovalent alcohols having 1 to 5 carbon atoms, divalent alcohols having 2 to 5 carbon atoms, and trivalent alcohols having 3 carbon atoms.

Specific examples of such alcohols include monovalent alcohols such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, and 4-methylcyclohexanol; divalent alcohols such as 1,2-ethanediol, 1,2-propanediol, 1,3-propanediol, 1,2-butanediol, 1,3-butanediol, 1,4-butanediol, 2,3-butanediol, and 1,5-pentanediol; and trivalent alcohols such as glycerin.

Preferred monovalent alcohols include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol, and 4-methylcyclohexanol. More preferred examples include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, and cyclohexanol. Still more preferred examples include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, and neopentyl alcohol. Particularly preferred examples include methanol, ethanol, 1-propanol, 2-propanol, 1-butanol, 2-butanol, isobutyl alcohol, 2-methyl-1-butanol, and isopentyl alcohol, and most preferred is ethanol.

Preferred divalent alcohols include 1,2-ethanediol, 1,2-propanediol, and 1,3-propanediol, and most preferred is 1,2-ethanediol. The trivalent alcohol is preferably glycerin.

The hydrocarbons are not particularly limited, and examples thereof include aliphatic hydrocarbons, aromatic hydrocarbons, and halogenated hydrocarbons. Preferred among these are aliphatic hydrocarbons and aromatic hydrocarbons, and more preferred are aliphatic hydrocarbons.

The aliphatic hydrocarbons are not particularly limited, and may be cyclic or acyclic, saturated or unsaturated aliphatic hydrocarbons. In general, saturated aliphatic hydrocarbons are preferred. The number of carbon atoms of the aliphatic hydrocarbon is typically 3 to 20, preferably 5 to 12, and more preferably 5 to 8. Specific examples include propane, butane, isobutane, pentane, 2-methylbutane, hexane, 2-methylpentane, 2,2-dimethylbutane, 2,3-dimethylbutane, heptane, isomers of heptane (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, and cyclohexene. Preferred examples include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, and p-menthane. More preferred examples include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, and ethylcyclohexane. Still more preferred examples include pentane, hexane, cyclohexane, and methylcyclohexane. Particularly preferred are heptane and methylcyclohexane, and most preferred is heptane, in terms of providing a particularly high oxidation-preventing effect.

The aromatic hydrocarbons are not particularly limited. The number of carbon atoms thereof is typically 6 to 20, preferably 6 to 12, and more preferably 7 to 10. Specific examples include benzene, toluene, xylenes, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene dodecylbenzene, and styrene. Preferred examples include toluene, xylenes, o-xylene, m-xylene, p-xylene, ethylbenzene, cumene, mesitylene, tetralin, butylbenzene, p-cymene, cyclohexylbenzene, diethylbenzene, and pentylbenzene. More preferred examples include toluene, xylenes, o-xylene, m-xylene, p-xylene, cumene, and tetralin. Most preferred is cumene.

The halogenated hydrocarbons are not particularly limited, and may be cyclic or acyclic, saturated or unsaturated halogenated hydrocarbons. In general, acyclic halogenated hydrocarbons are preferred. More preferred are chlorinated hydrocarbons and fluorinated hydrocarbons, and still more preferred are chlorinated hydrocarbons. The number of carbon atoms of the halogenated hydrocarbon is suitably 1 to 6, preferably 1 to 4, and more preferably 1 to 2. Specific examples include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, and 1,1,1,2-tetrafluoroethane. Preferred examples include dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, and 1,1,1,2-tetrafluoroethane. More preferred examples include dichloromethane, chloroform, 1,2-dichloroethylene, trichloroethylene, chlorobenzene, and 1,1,1,2-tetrafluoroethane.

The ethers are not particularly limited, and may be cyclic or acyclic, saturated or unsaturated ethers. In general, saturated ethers are preferred. The number of carbon atoms of the ether is typically 3 to 20, preferably 4 to 12, and more preferably 4 to 8. Specific examples include diethyl ether, methyl tert-butyl ether, dipropyl ether, diisopropyl ether, dibutyl ether, dihexyl ether, ethyl vinyl ether, butyl vinyl ether, anisole, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol monobutyl ether. Preferred examples include diethyl ether, methyl tert-butyl ether, dipropyl ether, diisopropyl ether, dibutyl ether, dihexyl ether, anisole, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, and ethylene glycol monoethyl ether. More preferred examples include diethyl ether, methyl tert-butyl ether, anisole, dioxane, tetrahydrofuran, ethylene glycol monomethyl ether, and ethylene glycol monoethyl ether. Still more preferred examples include diethyl ether, methyl tert-butyl ether, and anisole, and most preferred is methyl tert-butyl ether.

As the organic solvent (B) in the present invention, the solvents mentioned above may, of course, be used alone, or two or more of these may be used in combination. The organic solvent (A) for washing and the organic solvent (B) for extraction may be the same as or different from each other. The organic solvent (A) for washing and the organic solvent (B) for extraction are preferably the same in terms of collecting and reusing the used solvent. The organic solvent (A) for washing and the organic solvent (B) for extraction are most preferably both ethanol in terms of causing no problem with the residual solvent.

In the production method of the present invention, the amount of the organic solvent (B) used as an extraction solvent is not particularly limited. The use of an extremely large amount of the organic solvent (B) per dry cell weight, however, extremely reduces the carotenoid concentration in the resulting extract, making efficient refinement difficult. Conversely, the use of an extremely small amount of the organic solvent (B) per dry cell weight can provide a highly concentrated carotenoid extract; however, efficient extraction of a carotenoid contained in cells is extremely difficult considering the saturation solubility of the carotenoid in the organic solvent (B). From such viewpoints, in the production method of the present invention, the amount of the organic solvent (B) per part by dry weight of cells is preferably 1 part by weight or more, more preferably 5 parts by weight or more, and most preferably 10 parts by weight or more. Though the upper limit is not particularly limited, it is preferably 1000 parts by weight or less, more preferably 500 parts by weight or less, and most preferably 300 parts by weight or less.

In the production method of the present invention, the temperature for extraction with the organic solvent (B) is 10° C. to 70° C., preferably 20° C. or higher, more preferably 25° C. or higher, and particularly preferably 35° C. or higher. Also, the temperature is preferably 60° C. or lower, and more preferably 50° C. or lower. The extraction efficiency is improved as the temperature for extraction is raised; however, a temperature higher than 70° C. may cause the problem of transformation of the structure of a carotenoid, such as conversion of part of astaxanthin in the extracted carotenoid to the cis form. Conversely, extraction at a temperature lower than 10° C., at which the solubility of a carotenoid in the organic solvent (B) is low, is less likely to provide a sufficient yield.

In the extraction with the organic solvent (B) in the production method of the present invention, the method for mixing the organic solvent (B) with the yeast of the genus *Xanthophyllomyces* is not particularly limited, and examples thereof include a method using a device for disruption and emulsification, such as an impeller, a static mixer, a pump, a high-pressure homogenizer, a rotating blade homogenizer, or a ultrasonic homogenizer. Of course, extraction can be performed using two or more of these devices in combination.

In the production method of the present invention, the method for extraction may either be batch extraction or continuous extraction, or these extraction operations may be repeated multiple times. Continuous extraction is industrially preferred in terms of productivity. Especially, multistage countercurrent extraction is preferred as a continuous extraction method. The time for stirring in batch extraction is typically 5 minutes or longer, although it is not particularly limited. The average residence time in continuous extraction is typically 10 minutes or longer, although it is not particularly limited. The number of batch extraction stages is not particularly limited either. Although the use of a single extraction stage can provide efficient extraction, repeating extraction two or more times is preferred from the viewpoint of the yield.

In the production method of the present invention, before the extraction with the organic solvent (B), the washed yeast of the genus *Xanthophyllomyces* is preferably heat-treated while in contact with the organic solvent (B) to be used for the extraction, because this improves the extraction efficiency in the subsequent extraction process and thus can greatly reduce the amount of the organic solvent (B) used for extraction. The amount of the organic solvent (B) used in the heat treatment to provide the effect may be a part, for example, about 10-70%, of the total amount of the organic solvent (B) used for extraction. More specifically, the organic solvent (B) in an amount of 1 to 50 parts by weight or more, more preferably about 5 to 30 parts by weight, per part by dry weight of cells may preferably be used in the heat treatment. The temperature for the heat treatment is not particularly limited as long as it is 40° C. or higher, and it is preferably 50° C. to 80° C. The heating time is not particularly limited either, and it is preferably 1 to 120 minutes, and more preferably 15 to 60 minutes. The method for heating is not particularly limited either, and may be a method in which after washing the yeast of the genus *Xanthophyllomyces* with the organic solvent (A), the organic solvent (B) heated to a predetermined temperature is added thereto, or a method in which after adding the organic solvent (B) at ordinary temperature, the mixture is heated to a predetermined temperature. In the heating, the organic solvent (B) and the yeast of the genus *Xanthophyllomyces* may be left to stand still or may be stirred. Preferably, they are appropriately stirred. In this case, the method for stirring is not particularly limited, and the mixing method and/or device to be used in the extraction are directly applicable. In the production method of the present invention, after the heat treatment, the subsequent extraction may be performed after removing a part or the entire amount of the organic solvent (B) used in the heat treatment. Or, the subsequent extraction is preferably sequentially performed without subjecting the heat-treated mixture of the organic solvent (B) and the yeast of the genus *Xanthophyllomyces* to separation. In the extraction, the organic solvent (B) may optionally be further added in an amount necessary for the extraction (namely, the total of the amount of the organic solvent (B) remaining after the heat treatment and the amount of the organic solvent (B) optionally added after the heat treatment constitutes the amount of the organic solvent (B) used for the extraction). If the temperature for the heat treatment is higher than that for extraction, the subsequent extraction may be performed after cooling to a desired temperature.

After completing extraction of a carotenoid with the organic solvent (B), the yeast of the genus *Xanthophyllomyces* is separated from the organic solvent (B). The method for separation is not particularly limited, and a typical method such as pressure filtration, vacuum filtration, natural filtration, centrifugation, or decantation may be employed. Of course, two or more of these methods may be employed in combination.

The production method of the present invention enables highly efficient extraction of a carotenoid such as astaxanthin contained in the yeast of the genus *Xanthophyllomyces*, and the extraction ratio is typically 50% or higher, more preferably 70% or higher, and still more preferably 80% or higher.

In the production method of the present invention, the carotenoid extract obtained as above may be directly used as a carotenoid composition or may be appropriately processed into a carotenoid composition. The form of the carotenoid composition obtained by the production method of the present invention is not particularly limited, and is preferably an oily composition or powdered composition obtained as mentioned below.

The oily composition may be prepared by concentrating the carotenoid extract extracted with the organic solvent (B). The method for this concentration is not particularly limited, and applicable methods include vacuum concentration in a tank, flash concentration, and thin-film concentration.

The concentration is preferably performed until the organic solvent (A) or organic solvent (B) in the oily composition is sufficiently removed. The residual concentration of the organic solvent (A) and organic solvent (B) in the oily composition is not particularly limited unless it adversely affects human bodies when the composition is taken as food, a cosmetic or drug. The residual concentration in the oily composition is preferably 1% by weight or less, more preferably 0.1% by weight or less, and still more preferably 0.01% by weight or less.

The temperature condition for the concentration is not particularly limited unless it remarkably causes decomposition and transformation (e.g. conversion to the cis form) of a carotenoid during the concentration. The temperature is preferably 10° C. to 80° C., more preferably 20° C. to 70° C., and still more preferably 25° C. to 60° C. In the present invention, the concentration may be performed under reduced pressure as needed.

In the production method of the present invention, if a concentrate resulting from the concentration is in an oily form, the concentrate may be directly used as an oily composition. If the concentrate is obtained as a dry solid, and from the viewpoint of handleability of the final product, a target oily composition may be prepared by adding a liquid oil or fat to the concentrate and mixing them. The term "oily composition" used herein includes a slurry form in which a carotenoid is partially precipitated, in addition to an oily form in which a carotenoid and other components are uniformly mixed.

The liquid oil or fat that may be added is not particularly limited as long as it dissolves or disperses the concentrate of a carotenoid such as astaxanthin. For example, it may be a natural fat or oil from animals or vegetables, or a synthesized or processed fat or oil. More preferred are those acceptable for use in food, cosmetics or drugs. Examples of vegetable fats and oils include coconut oil, palm oil, palm kernel oil, linseed oil, camellia oil, brown rice germ oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, and olive oil. Examples of animal fats and oils include lard, milk fat, fish oil, and beef tallow. In addition, processed fats and oils prepared from these fats and oils by separation, hydrogenation, transesterification, and the like (e.g. hydrogenated oil) may also be used. Of course, medium-chain triglycerides (MCT) may also be used. Moreover, mixtures of these may also be used. Examples of medium-chain triglycerides include triglycerides whose fatty acid has 6 to 12 carbon atoms, and preferably 8 to 12 carbon atoms.

Preferred examples of these fats and oils include vegetable fats and oils, synthesized fats and oils, and processed fats and oils, in terms of easy handling, odor and the like. More preferred specific examples include coconut oil, palm oil, palm kernel oil, rapeseed oil, rice oil, soybean oil, cottonseed oil, safflower oil, olive oil, and MCT.

After the concentrate of the carotenoid extract is prepared, the liquid oil or fat may be added and mixed to prepare a target oily composition of a carotenoid. Or, the liquid oil or fat may be added before or during the extraction or concentration, followed by the subsequent treatments.

The carotenoid content in the carotenoid-containing oily composition of the present invention is not particularly limited, and may be appropriately set according to the requirements of a target product. For example, if astaxanthin is targeted as the carotenoid, the upper limit of the astaxanthin content in the oily composition is preferably 30% by weight or less, more preferably 20% by weight or less, and still more preferably 15% by weight or less, in terms of preparing an oily composition with easily handleable viscosity and appearance. The lower limit of the astaxanthin content in the oily composition is not particularly limited, and is preferably 0.1% by weight or more, more preferably 1% by weight or more, and still more preferably 3% by weight or more.

In particular, the production method of the present invention enables preparation of an oily composition with a small amount of ergosterol derived from the yeast of the genus *Xanthophyllomyces*. For example, the oily composition produced by the method of the present invention has a ratio of ergosterol content to astaxanthin content [(ergosterol content)/(astaxanthin content)] of 40% by weight or lower. That is, the carotenoid-containing oily composition, which contains astaxanthin derived from a yeast of the genus *Xanthophyllomyces* and has a ratio of ergosterol content to astaxanthin content of 40% by weight or lower, is also within the scope of the present invention, regardless of the method used to produce it. The ratio of ergosterol content is preferably 35% by weight or lower, and more preferably 30% by weight or lower. The ratio of ergosterol content to astaxanthin content can be determined by high-performance liquid chromatography or the like.

In addition, not only does the production method of the present invention enable easy preparation of an oily composition with a high astaxanthin content, but also the oily composition characteristically has a quite low viscosity and good handleability as compared with prior art oily compositions containing astaxanthin derived from a yeast of the genus *Xanthophyllomyces*. For example, a preferred method of the present invention enables preparation of an unprecedented highly concentrated carotenoid-containing oily composition with a low viscosity, which has an astaxanthin content of 1 to 20% by weight and a viscosity at a temperature of 30° C. and a shear rate of 100 $s^{-1}$ of 0.01 to 1 Pa·s, preferably 0.01 to 0.7 Pa·s. That is, the carotenoid-containing oily composition, which contains astaxanthin derived from a yeast of the genus *Xanthophyllomyces* and has an astaxanthin content of 1 to 20% by weight and a viscosity at a temperature of 30° C. and a shear rate of 100 $s^{-1}$ of 0.01 to 1 Pa·s, preferably 0.01 to 0.7 Pa·s, is also within the scope of the present invention, regardless of the method used to produce it.

Moreover, the carotenoid composition produced by the method of the present invention has been found to be absorbed at a higher rate in vivo than prior art carotenoid compositions derived from a yeast of the genus *Xanthophyllomyces*.

Meanwhile, the production method of the present invention also enables preparation of, as a carotenoid composition, a powdered composition with a high astaxanthin content by treating the carotenoid extract extracted with the organic solvent (B) by, for example, concentration and/or cooling to precipitate a carotenoid and then subjecting the resulting precipitate to solid-liquid separation.

Regarding the extraction of a carotenoid from the yeast of the genus *Xanthophyllomyces*, if washing with an organic solvent is not performed before the extraction, concentration of the resulting extract only provides a viscous concentrate and fails to precipitate the carotenoid to separate it. Even washing of this concentrate with ethanol or the like as mentioned in, for example, Patent Literatures 5 and 6 cannot provide crystals of the carotenoid, especially of astaxanthin. Thus, in the production method of the present invention, particularly for the sake of forming a powdered carotenoid composition, the order in which washing with the organic solvent (A) is performed before the extraction with the organic solvent (B) is important.

In the production method of the present invention, the method for precipitating a carotenoid is not particularly limited, and examples thereof include a method of performing evaporation crystallization on an extract while concentrating it; a method of adding a poor solvent for a carotenoid to an extract as it is obtained, or to an appropriately concentrated extract, to precipitate a carotenoid; and a method of cooling an extract as it is obtained, or an appropriately concentrated extract, so that the saturation solubility of a carotenoid is exceeded to crystallize the carotenoid. Of course, these methods may be used in combination in the production method of the present invention. From the viewpoint of the yield and operability, it is desirable to concentrate the extract until a certain amount of crystals of carotenoid is precipitated and then add a poor solvent thereto or cool the concentrate to precipitate the carotenoid.

In the concentration of the extract in the preparation of a powdered composition, if the concentration ratio of the extract is too low, a target carotenoid mostly remains dissolved in the mother liquor, which reduces the total amount of the powdered composition to be prepared, and thus tends not to provide a sufficient yield and productivity. Conversely, if the concentration ratio of the extract is too high, precipitation of contaminants derived from the yeast of the genus *Xanthophyllomyces* other than carotenoids becomes significant, which unfortunately reduces the astaxanthin content in the powdered composition to be prepared. Thus, in the preparation of a powdered composition, the extract should be concentrated to a proper concentration ratio to achieve a sufficient yield, productivity, and content. For example, the extract is preferably concentrated to a concentration ratio of 10 to 1000, more preferably 50 to 500.

In the preparation of a powdered composition, the above precipitation is followed by solid-liquid separation of the resulting precipitate from the organic solvent used for the extraction. Any typical solid-liquid separation method may be used in the solid-liquid separation, and examples thereof include decantation, centrifugation, pressure filtration, vacuum filtration, and natural filtration. Further, the resulting cake may optionally be washed, and then dried for example under vacuum to remove the residual organic solvent and the like, thus obtaining a dry powder of a carotenoid composition.

Astaxanthin is known to exist in two crystal polymorphic forms: Form I having a powder X-ray diffraction pattern including strong peaks at diffraction angles of 13.3° (2θ±0.2°), 13.8° (2θ±0.2°), 14.3° (2θ±0.2°), 15.8° (2θ±0.2°), 16.3° (2θ±0.2°), 18.2° (2θ±0.2°), 20.5° (2θ±0.2°), 24.8° (2θ±0.2°), and 25.3° (2θ±0.2°); and Form II with strong peaks at diffraction angles of 12.2° (2θ±0.2°), 13.2° (2θ±0.2°), 13.5° (2θ±0.2°), 16.1° (2θ±0.2°), 16.6° (2θ±0.2°), 20.1° (2θ±0.2°), 21.3° (2θ±0.2°), 22.7° (2θ±0.2°), 24.6° (2θ±0.2°), and 27.5° (2θ±0.2°). The powdered composition produced by the method of the present invention has been found to have a powder X-ray diffraction pattern including strong peaks at diffraction angles of 13.3° (2θ±0.2°), 13.8° (2θ±0.2°), 14.3° (2θ±0.2°), 15.8° (2θ±0.2°), 16.3° (2θ±0.2°), 18.2° (2θ±0.2°), 20.5° (2θ±0.2°), 24.8° (2θ±0.2°), and 25.3° (2θ±0.2°). In other words, the powdered composition produced by the method of the present invention is considered as a carotenoid composition containing a large amount of crystal Form I of astaxanthin. Further, the astaxanthin in the carotenoid composition produced by the method of the present invention is derived from the genus *Xanthophyllomyces* and has a chemical structure of (3R, 3'R). There have been no reports of a powdered composition containing a large amount of astaxanthin which is derived form a yeast of the genus *Xanthophyllomyces* and has such a crystal form and such a chemical structure. Thus, the carotenoid composition, which contains astaxanthin that has a powder X-ray diffraction pattern including strong peaks at diffraction angles of 13.3° (2θ±0.2°), 13.8° (2θ±0.2°), 14.3° (2θ±0.2°), 15.8° (2θ±0.2°), 16.3° (2θ±0.2°), 18.2° (2θ±0.2°), 20.5° (2θ±0.2°), 24.8° (2θ±0.2°), and 25.3° (2θ±0.2°), and has a chemical structure of (3R, 3'R), is also within the scope of the present invention, regardless of the method used to produce it.

In the production method of the present invention, washing the cells with the organic solvent (A) in the production process removes most of the contaminants derived from the yeast of the genus *Xanthophyllomyces*, such as lipids. Thus, a powdered composition obtained as the carotenoid composition is excellent in powder flowability. Specifically, the powdered composition produced by a preferred method of the present invention is in a powder form with a Dr. Carr's flowability index of 60 or higher. A higher value of the index is more preferred from the viewpoint of powder flowability. Appropriate selection of the preferred production conditions mentioned above can provide a powdered composition with an index of 70 or higher, or even 80 or higher. In contrast, an astaxanthin-containing powdered composition prepared according to Patent Literature 7 has a Dr. Carr's flowability index of lower than 60 and thus has poor flowability and causes problems in productivity and operability, such as deterioration of delivery efficiency of the carotenoid powder and incapability of smooth filling of a device with the powder. Thus, the astaxanthin-containing carotenoid composition, which is in a powder form with a Dr. Carr's flowability index of 60 or higher, is also a preferred aspect of the carotenoid composition of the present invention.

The Dr. Carr's flowability index of powders is an index based on the overall evaluation of the angle of repose, compressibility, angle of spatula, and uniformity of particles, and is defined in CHEMICAL ENGINEERING, January 18 (1965). Table 1 shows the definition details of the powder flowability index.

TABLE 1

| Flow characteristics | Flow/ability index (total points in right columns) | Angle of repose (°) | Point | Compressibility (%) | Point | Angle of spatula (°) | Point | Uniformity (unit) | Point |
| --- | --- | --- | --- | --- | --- | --- | --- | --- | --- |
| Excellent | 90 to 100 | <25 | 25 | <5 | 25 | <25 | 25 | 1 | 25 |
|  |  | 26-29 | 24 | 6-9 | 23 | 26-30 | 24 | 2-4 | 23 |
|  |  | 30 | 22.5 | 10 | 22.5 | 31 | 22.5 | 5 | 22.5 |
| Good | 80 to 89 | 31 | 22 | 11 | 22 | 32 | 22 | 6 | 22 |
|  |  | 32-34 | 21 | 12-14 | 21 | 33-37 | 21 | 7 | 21 |
|  |  | 35 | 20 | 15 | 20 | 38 | 20 | 8 | 20 |
| Fair | 70 to 79 | 36 | 19.5 | 16 | 19.5 | 39 | 19.5 | 9 | 19 |
|  |  | 37-39 | 18 | 17-19 | 18 | 40-44 | 18 | 10-11 | 18 |
|  |  | 40 | 17.5 | 20 | 17.5 | 45 | 17.5 | 12 | 17.5 |
| Passable | 60 to 69 | 41 | 17 | 21 | 17 | 46 | 17 | 13 | 17 |
|  |  | 42-44 | 16 | 22-24 | 16 | 47-59 | 16 | 15-16 | 16 |
|  |  | 45 | 15 | 25 | 15 | 60 | 15 | 17 | 15 |
| Poor | 40 to 59 | 46 | 14.5 | 26 | 14.5 | 61 | 14.5 | 18 | 14.5 |
|  |  | 47-54 | 12 | 27-30 | 12 | 62-74 | 12 | 19-21 | 12 |
|  |  | 55 | 10 | 31 | 10 | 75 | 10 | 22 | 10 |
| Very Poor | 20 to 39 | 56 | 9.5 | 32 | 9.5 | 76 | 9.5 | 23 | 9.5 |
|  |  | 57-64 | 7 | 33-36 | 7 | 77-89 | 7 | 24-26 | 7 |
|  |  | 65 | 5 | 37 | 5 | 90 | 5 | 27 | 5 |
| Very, very poor | 0 to 19 | 66 | 4.5 | 38 | 4.5 | 91 | 4.5 | 28 | 4.5 |
|  |  | 67-89 | 2 | 39-45 | 2 | 92-99 | 2 | 29-35 | 2 |
|  |  | 90 | 0 | >45 | 0 | >99 | 0 | >35 | 0 |

The astaxanthin content in the powdered composition produced by the method of the present invention is preferably 20 to 80% by weight, more preferably 30 to 80% by weight, and still more preferably 40 to 80% by weight. It is practically difficult for conventional methods to prepare such a powdered composition containing a high concentration of astaxanthin derived from a yeast of the genus *Xanthophyllomyces* and a small amount of contaminants. That is, the powdered composition, which contains astaxanthin derived from a yeast of the genus *Xanthophyllomyces* and has an astaxanthin content of 20 to 80% by weight, is another preferred aspect of the carotenoid composition of the present invention.

EXAMPLES

The present invention is more specifically described referring to examples that are not intended to limit the present invention.
(High-Performance Liquid Chromatography Analysis Conditions)
Column: FinePak SIL C18T-5, 4.6×250 mm (product of JASCO Corporation)
Mobile phase: acetonitrile/ethyl acetate/formic acid/distilled water=600/300/60/40

Flow rate: 0.8 mL/min
Detection wavelength: 471 nm
(Gas Chromatography Analysis Conditions)
Column: J&W DB-624, 30 m×0.32 mm, film thickness 1.8 μm (product of Agilent Technologies)
Gas: He (70 kPa), Air (50 kPa), $H_2$ (60 kPa)
Detection: FID
(Viscosity Measurement Conditions)
Apparatus: AR-G2 produced by TA Instruments
Shear rate: 10 to 1000 $s^{-1}$
Cone: 40 mm 2° aluminum cone
Temperature: 30° C.
(Powder X-Ray Diffraction Measurement Conditions)
Apparatus: MiniFlex II produced by Rigaku Corporation
X-ray used: Cu/Kα radiation, X-ray intensity: 30 kV, 15 mA, Angle range: 2θ=2 to 60°
Scanning rate: 2°/min
Sampling interval: 0.02°
Divergence slit: 1.25°
Scattering slit: 1.25°
Ethanol used in the examples was absolute ethanol with a purity of at least 99.5 w/w % (specific gravity: about 0.79), and all other organic solvents were of reagent grade.

Synthesis Example 1

An amount of 5 mL of a YM medium (containing 0.5% of polypeptone, 0.3% of yeast extract, 0.3% of malt extract, and 1.0% of glucose) was placed in each of four test tubes and inoculated with the KNK-11 strain, which was a mutant strain prepared by mutagenesis of *Xanthophyllomyces dendrorhous* NBRC 10129 (available from Biological Resource Center, National Institute of Technology and Evaluation (2-5-8 Kazusa-Kamatari, Kisarazu-shi, Chiba, 292-0818, Japan)) with NTG. The strain was incubated at 20° C. for 48 hours. The culture fluids were transferred to four 500-mL sakaguchi flasks each containing 50 mL of a YM medium, followed by incubation at 20° C. for 48 hours. The culture fluids were transferred to a 5000-mL jar fermenter containing 2500 mL of a medium (containing 1.3% of ammonium phosphate, 0.7% of potassium phosphate, 0.3% of yeast extract, and 1% of glucose) and the strain was incubated at 20° C., thus obtaining a cell-containing culture fluid containing astaxanthin and HDCO. During the incubation, pH was controlled to a range of 4.4 to 5.6, and glucose was added in fed-batch mode so that the dissolved oxygen level was 30 to 80% of the saturation value.

To 3000 mL of the resulting culture fluid was added 400 g of sulfuric acid, and the mixture was stirred at 70° C. for 1 hour. Then, 1300 g of 30% sodium hydroxide was added to neutralize the culture fluid, 150 g of celite as a filter aid was mixed with the resulting culture fluid, and the mixture was vacuum filtered to prepare wet cells (water content: 60% by weight, cell content: 20% by weight (dry weight)).

Example 1

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 800 mL (632 g) of ethanol and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to $\frac{1}{100}$, 1.63 g of safflower oil was then added thereto, and concentration of the mixture was further continued. The resulting oily material (2.5 g) had an astaxanthin content of 4.0% by weight. The residual ethanol content in the oily material was determined by gas chromatography and found to be 0.1% by weight. The oily material had a ratio of ergosterol content to astaxanthin content (=(ergosterol content)/(astaxanthin content); the same shall apply hereinafter) of 33.0% by weight and a viscosity at a temperature of 30° C. and a shear rate of 100 $s^{-1}$ of 0.30 Pa·s.

Example 2

To 646 kg of the wet cells (containing 2.58 kg of astaxanthin) prepared as in Synthesis Example 1 was added 2000 L (1580 kg) of ethanol cooled to 8° C., and the mixture was stirred at the same temperature for 30 minutes. The resulting mixture was pressure filtered to obtain a cake-1 and a filtrate-1. The astaxanthin concentration of the filtrate-1 was determined by high-performance liquid chromatography and found to be 0.005% by weight. To the cake-1 was added 16000 L (12640 kg) of ethanol, and the mixture was stirred at room temperature for 1 hour. The resulting mixture was pressure filtered to obtain a cake-2 and a filtrate-2. To the cake-2 was further added 16000 L (12640 kg) of ethanol, and the mixture was stirred at 40° C. for 1 hour. The resulting mixture was pressure filtered to obtain a cake-3 and a filtrate-3. The filtrate-2 and filtrate-3 were combined and the resulting liquid contained 2.13 kg of astaxanthin. This liquid was vacuum concentrated until the amount thereof was reduced to $\frac{1}{100}$, 32.6 kg of safflower oil was then added thereto, and concentration of the mixture was further continued. The resulting oily material (50.0 kg) had an astaxanthin content of 4.2% by weight. The residual ethanol content in the oily material was determined by gas chromatography and found to be 0.04% by weight. The oily material had a ratio of ergosterol content to astaxanthin content of 29.5% by weight and a viscosity at a temperature of 30° C. and a shear rate of 100 $s^{-1}$ of 0.33 Pa·s.

Example 3

To 32.3 g of the wet cells (containing 0.13 g of astaxanthin) obtained in Synthesis Example 1 was added 50 mL (39.5 g) of acetone cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.03% by weight. To the cake-1 was added 800 mL (632 g) of ethanol, and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.10 g of astaxanthin. This liquid was vacuum concentrated until the amount thereof was reduced to $\frac{1}{100}$, 1.63 g of safflower oil was then added thereto, and concentration of the mixture was further continued. The resulting oily material (2.5 g) had an astaxanthin content of 3.6% by weight. The residual ethanol content in the oily material was determined by gas chromatography and found to be 0.2% by weight. The oily material had a ratio of ergosterol content to astaxanthin content of 38.3% by weight and a viscosity at a temperature of 30° C. and a shear rate of 100 s$^{-1}$ of 0.62 Pa·s.

Example 4

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 800 mL (614 g) of ethanol containing 20% by volume of n-heptane, and the mixture was stirred at 40° C. for 1 hour. The resulting mixture was vacuum filtered to obtain a cake-2 and a filtrate-2. To the cake-2 was further added 800 mL (614 g) of ethanol containing 20% by volume of n-heptane, and the mixture was stirred at 40° C. for 1 hour. The resulting mixture was vacuum filtered to obtain a cake-3 and a filtrate-3. The filtrate-2 and filtrate-3 were combined and the resulting liquid contained 0.09 g of astaxanthin. This liquid was vacuum concentrated until the amount thereof was reduced to 1/100, 1.63 g of safflower oil was then added thereto, and concentration of the mixture was further continued. The resulting oily material (2.5 g) had an astaxanthin content of 3.2% by weight. The residual n-heptane content and the residual ethanol content in the oily material were determined by gas chromatography and each found to be 0.1% by weight or lower. The oily material had a ratio of ergosterol content to astaxanthin content of 32.0% by weight and a viscosity at a temperature of 30° C. and a shear rate of 100 s$^{-1}$ of 0.40 Pa·s.

Example 5

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 1600 mL (1264 g) of ethanol and the mixture was stirred at 40° C. for 1 hour. The resulting mixture was vacuum filtered to obtain a cake-2 and a filtrate-2. The filtrate-2 contained 0.11 g of astaxanthin. This filtrate was vacuum concentrated until the amount thereof was reduced to 1/100, 1.63 g of safflower oil was then added thereto, and concentration of the mixture was further continued. The resulting oily material (2.5 g) had an astaxanthin content of 4.0% by weight. The residual ethanol content in the oily material was determined by gas chromatography and found to be 0.1% by weight. The oily material had a ratio of ergosterol content to astaxanthin content of 32.2% by weight and a viscosity at a temperature of 30° C. and a shear rate of 100 s$^{-1}$ of 0.26 Pa·s.

Example 6

To 32.3 g of the wet cells (containing 0.13 g of astaxanthin) obtained in Synthesis Example 1 was added 50 mL (39.5 g) of methanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.018% by weight. To the cake-1 was added 800 mL (632 g) of 2-propanol, and the mixture was stirred at 40° C. for 1 hour. The resulting mixture was vacuum filtered to obtain a cake-2 and a filtrate-2. To the cake-2 was further added 800 mL (632 g) of 2-propanol and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to 1/100, 1.63 g of MCT was then added thereto, and concentration of the mixture was further continued. The resulting oily material (2.5 g) had an astaxanthin content of 3.9% by weight. The residual 2-propanol content in the oily material was determined by gas chromatography and found to be 0.1% by weight. The oily material had a ratio of ergosterol content to astaxanthin content of 28.6% by weight and a viscosity at a shear rate of 100 s$^{-1}$ of 0.18 Pa·s.

Example 7

To 32.3 g of the wet cells (dry weight: 12.9 g, containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 200 mL (158 g) of ethanol, and the mixture was stirred at 60° C. for 30 minutes. Then, 400 mL (316 g) of ethanol was further added thereto and the mixture was stirred at 40° C. for 1 hour. The resulting mixture was vacuum filtered to obtain a cake-2 and a filtrate-2. The filtrate-2 contained 0.11 g of astaxanthin. This filtrate was vacuum concentrated until the amount thereof was reduced to 1/100, 1.63 g of safflower oil was then added thereto, and concentration of the mixture was further continued. The resulting oily material (2.5 g) had an astaxanthin content of 3.9% by weight. The residual ethanol content in the oily material was determined by gas chromatography and found to be 0.1% by weight.

Example 8

An amount of 5 mL of a YM medium (containing 0.5% of polypeptone, 0.3% of yeast extract, 0.3% of malt extract, and 1.0% of glucose) was placed in each of four test tubes and inoculated with *Xanthophyllomyces dendrorhous* NBRC 10129 (available from Biological Resource Center, National Institute of Technology and Evaluation (2-5-8 Kazusa-Kamatari, Kisarazu-shi, Chiba, 292-0818, Japan)), and the strain was incubated at 20° C. for 48 hours. The culture fluids were transferred to four 500-mL sakaguchi flasks each containing 50 mL of a YM medium, and the strain was incubated at 20° C. for 48 hours. The resulting culture fluids were transferred to a 5000-mL jar fermenter containing 2500 mL of a medium (containing 1.3% of ammonium phosphate, 0.7% of potassium phosphate, 0.3% of yeast extract, and 1% of glucose), and the strain was incubated at 20° C. During the incubation, the pH was controlled to a range of 4.4 to 5.6, and glucose was added in fed-batch mode so that the dissolved oxygen level was 30 to 80% of the saturation value.

To 3000 mL of the resulting culture fluid was added 400 g of sulfuric acid, and the mixture was stirred at 70° C. for 1 hour. Then, 1300 g of 30% sodium hydroxide was added to neutralize the culture fluid, 150 g of celite as a filter aid was mixed with the resulting culture fluid, and the resulting mixture was vacuum filtered to prepare wet cells (water content: 58% by weight, cell content: 21% by weight (dry weight)).

To 500 g of the thus obtained wet cells (containing 0.006 g of astaxanthin) was added 1400 mL (1106 g) of ethanol cooled to 10° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.0001% by weight. To the cake-1 was added 1400 mL (1106 g) of ethanol cooled to 10° C., and the mixture was stirred at the same temperature for 30 minutes. The resulting mixture was vacuum filtered to obtain a cake-2 and a filtrate-2. The astaxanthin concentration of the filtrate-2 was 0.0001% by weight. To the cake-2 was added 15000 mL (11850 g) of ethanol, and the mixture was stirred at 40° C. for 1 hour. The resulting mixture was vacuum filtered to obtain a cake-3 and a filtrate-3. The filtrate-3 contained 0.0032 g of astaxanthin. This filtrate was vacuum concentrated until the amount thereof was reduced to $1/1000$, 0.5 g of safflower oil was then added thereto, and concentration of the mixture was further continued. The resulting oily material (1.0 g) had an astaxanthin content of 0.3% by weight. The residual ethanol content in the oily material was determined by gas chromatography and found to be 0.1% by weight.

Example 9

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 800 mL (632 g) of ethanol, and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to $1/100$, the concentrate was vacuum filtered to separate solids from the liquid, and the solids were vacuum dried at room temperature to give a black purple powder. The powder (0.20 g) had an astaxanthin content of 51.4% by weight. The powder was measured by powder X-ray diffraction and found to have crystal Form I. The powder was evaluated for powder flowability using a powder tester (Powder Tester PT-R, produced by Hosokawa Micron Corporation; the same shall apply hereinafter) and found to have a Dr. Carr's flowability index of 81 with a rating of "Good" in terms of flowability characteristics.

Example 10

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 800 mL (632 g) of ethanol, and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to $1/150$, the resulting concentrate was vacuum filtered to separate solids from the liquid, and the solids were then vacuum dried at room temperature to give a black purple powder. The powder (0.21 g) had an astaxanthin content of 45.1% by weight. The powder was measured by powder X-ray diffraction and found to have crystal Form I. The powder was evaluated for powder flowability using a powder tester (Powder Tester PT-R, produced by Hosokawa Micron Corporation; the same shall apply hereinafter) and found to have a Dr. Carr's flowability index of 76 with a rating of "Fair" in terms of flowability characteristics.

Example 11

To 32.3 g of the wet cells (containing 0.13 g of astaxanthin) obtained in Synthesis Example 1 was added 100 mL (79 g) of ethanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.005% by weight. To the cake-1 was added 800 mL (632 g) of ethanol, and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to $1/50$, and the resulting concentrate was cooled to 5° C. The cooled concentrate was vacuum filtered to separate solids from the liquid, and the solids were then vacuum dried at room temperature to give a black purple powder. The powder (0.34 g) had an astaxanthin content of 30.7% by weight. The powder was measured by powder X-ray diffraction and found to have crystal Form I. The powder was evaluated for powder flowability using a powder tester (Powder Tester PT-R, produced by Hosokawa Micron Corporation; the same shall apply hereinafter) and found to have a Dr. Carr's flowability index of 64 with a rating of "Passable" in terms of flowability characteristics.

Example 12

To 32.3 g of the wet cells (containing 0.13 g of astaxanthin) obtained in Synthesis Example 1 was added 50 mL (39.5 g) of acetone cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.03% by weight. To the cake-1 was added 800 mL (632 g) of ethanol, and the mixture was stirred at 40° C. for 1 hour. The resulting mixture was vacuum filtered to obtain a cake-2 and a filtrate-2. To the cake-2 was further added 800 mL (632 g) of ethanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.10 g of astaxanthin. This liquid was vacuum concentrated until the amount thereof was reduced to 1/150, the resulting concentrate was vacuum filtered to separate solids from the liquid, and the solids were then vacuum dried at room temperature to give a black purple powder. The powder (0.20 g) had an astaxanthin content of 48.6% by weight. The powder was measured by powder X-ray diffraction and found to have crystal Form I. The powder was evaluated for powder flowability using a powder tester (Powder Tester PT-R, produced by Hosokawa Micron Corporation; the same shall apply hereinafter) and found to have a Dr. Carr's flowability index of 80 with a rating of "Good" in terms of flowability characteristics.

Example 13

To 32.3 g of the wet cells (containing 0.13 g of astaxanthin) obtained in Synthesis Example 1 was added 50 mL (39.5 g) of methanol cooled to 5° C., and the mixture was stirred at the same temperature for 30 minutes. The resulting mixture was vacuum filtered to obtain a cake-1 and a filtrate-1. The astaxanthin concentration of the filtrate-1 was determined by high-performance liquid chromatography and found to be 0.018% by weight. To the cake-1 was added 800 mL (632 g) of 2-propanol, and the mixture was stirred at 40° C. for 1 hour. The resulting mixture was vacuum filtered to obtain a cake-2 and a filtrate-2. To the cake-2 was further added 800 mL (632 g) of 2-propanol, and the mixture was stirred at 40° C. for 1 hour. The resulting mixture was vacuum filtered to obtain a cake-3 and a filtrate-3. The filtrate-2 and filtrate-3 were combined and the resulting liquid contained 0.11 g of astaxanthin. This liquid was vacuum concentrated until the amount thereof was reduced to 1/50, and the resulting concentrate was cooled to 5° C. The cooled concentrate was vacuum filtered to separate solids from the liquid, and the solids were then vacuum dried at room temperature to give a black purple powder. The powder (0.36 g) had an astaxanthin content of 28.8% by weight. The powder was measured by powder X-ray diffraction and found to have crystal Form I. The powder was evaluated for powder flowability using a powder tester (Powder Tester PT-R, produced by Hosokawa Micron Corporation; the same shall apply hereinafter) and found to have a Dr. Carr's flowability index of 64 with a rating of "Passable" in terms of flowability characteristics.

Comparative Example 1

To 32.3 g of the wet cells (containing 0.13 g of astaxanthin) obtained in Synthesis Example 1 was added 1600 mL (1264 g) of acetone, and the mixture was stirred at 40° C. for 1 hour. The resulting mixture was vacuum filtered to obtain a cake and a filtrate. The filtrate contained 0.12 g of astaxanthin. This filtrate was vacuum concentrated, 1.63 g of MCT was then added thereto, and concentration of the mixture was further continued. The resulting oily material (2.9 g) had an astaxanthin content of 3.5% by weight. The residual acetone content in the oily material was determined by gas chromatography and found to be 0.2% by weight. The oily material had a ratio of ergosterol content to astaxanthin content of 40.8% by weight and a viscosity at a temperature of 30° C. and a shear rate of 100 s$^{-1}$ of 3.2 Pa·s.

Comparative Example 2

To 32.3 g of the wet cells (containing 0.13 g of astaxanthin) obtained in Synthesis Example 1 was added 800 mL (632 g) of ethanol, and the mixture was stirred at 40° C. for 1 hour. The resulting mixture was vacuum filtered to obtain a cake-1 and a filtrate-1. To the cake-1 was further added 800 mL (632 g) of ethanol, and the mixture was stirred at 40° C. for 1 hour. The resulting mixture was vacuum filtered to obtain a cake-2 and a filtrate-2. The filtrate-1 and filtrate-2 were combined and the resulting liquid contained 0.11 g of astaxanthin. This liquid was vacuum concentrated, 1.63 g of MCT was then added thereto, and concentration of the mixture was further continued. The resulting oily material (3.6 g) had an astaxanthin content of 2.8% by weight. The residual ethanol content in the oily material was determined by gas chromatography and found to be 0.1% by weight. The oily material had a ratio of ergosterol content to astaxanthin content of 58.9% by weight and a viscosity at a temperature of 30° C. and a shear rate of 100 s$^{-1}$ of 2.1 Pa·s.

Comparative Example 3

To 32.3 g of the wet cells (containing 0.13 g of astaxanthin) obtained in Synthesis Example 1 was added 800 mL (632 g) of ethanol, and the mixture was stirred at 85° C. for 1 hour. The resulting mixture was vacuum filtered to obtain a cake and a filtrate. The filtrate contained 0.12 g of astaxanthin. After this filtrate was vacuum concentrated until the amount thereof was reduced to 1/100, the resulting concentrate was tried to be vacuum filtered for separation of a solid precipitate from the liquid. The precipitate, however, was greatly sticky, which prevented the filtration.

Comparative Example 4

An amount of 32.3 g of the wet cells (containing 0.13 g of astaxanthin) obtained in Synthesis Example 1 was freeze dried for 48 hours to give 15.8 g of dry cells. To the dry cells was added 400 mL (316 g) of acetone, and the mixture was stirred at room temperature for 3 hours. The resulting mixture was vacuum filtered to obtain a cake-1 and a filtrate-1. The cake-1 was suspended in 200 mL (158 g) of acetone, and then the mixture was vacuum filtered again to obtain a cake-2 and a filtrate-2. The filtrate-1 and filtrate-2 were combined and the resulting liquid contained 0.12 g of astaxanthin. This liquid was vacuum concentrated until the amount thereof was reduced to 1/13, and 10 g of deionized water was added to the resulting concentrate. The mixture was stirred, vacuum concentrated, and then left to stand still for separation. The separated water phase was removed, 50 g of hexane was added to the remaining phase, and the mixture was stirred and then vacuum filtered to separate solids from the liquid. The solids were suspended in 30 g of hexane, the mixture was vacuum filtered to separate solids from the liquid, and the solids were vacuum dried at room temperature to give a black purple powder. The powder (0.18 g) had an astaxanthin content of 50.7% by weight. The powder was measured by powder X-ray diffraction and found to have crystal Form II. The powder was evaluated for powder flowability using a powder tester (Powder Tester PT-R, produced by Hosokawa Micron Corporation; the same shall apply hereinafter) and found to have a Dr. Carr's flowability index of 53 with a rating of "Poor" in terms of flowability characteristics.

Table 2 shows the preparation conditions, the astaxanthin content in the obtained carotenoid oily material, the proportion (% by weight) of ergosterol to astaxanthin, and the viscosity of the oily material in each of Examples 1 to 6 and Comparative Examples 1 and 2. Table 3 shows the preparation conditions, the astaxanthin content in the obtained carotenoid powder, the crystal form of the powder, and the powder flowability index in each of Examples 9 to 13 and Comparative Examples 3 and 4.

seconds to deproteinize it. Next, 4 mL of n-hexane was added and the mixture was mixed for 5 minutes with a shaker. The resulting mixture was centrifuged (3000 rpm×10 min), and

TABLE 2

| | Washing | Extraction | | | | | (Ergosterol content)/ | Viscosity |
|---|---|---|---|---|---|---|---|---|
| | Organic solvent (A) | Organic solvent (B) | Number of extraction stages | Liquid oil or fat | Appearance | Astaxanthin content weight % | (Astaxanthin content) weight % | (30° C., 100 s$^{-1}$) Pa · s |
| Example 1 | Ethanol | Ethanol | 2 | Safflower oil | Oily | 4.0 | 33.0 | 0.30 |
| Example 2 | Ethanol | Ethanol | 2 | Safflower oil | Oily | 4.2 | 29.5 | 0.33 |
| Example 3 | Acetone | Ethanol | 2 | Safflower oil | Oily | 3.6 | 38.3 | 0.62 |
| Example 4 | Ethanol | Ethanol/Heptane = 80/20 | 2 | Safflower oil | Oily | 3.2 | 32.0 | 0.40 |
| Example 5 | Ethanol | Ethanol | 1 | Safflower oil | Oily | 4.0 | 32.2 | 0.26 |
| Example 6 | Methanol | 2-Propanol | 2 | MCT | Oily | 3.9 | 28.6 | 0.18 |
| Comparative Example 1 | — | Acetone | 1 | MCT | Oily | 3.5 | 40.8 | 3.2 |
| Comparative Example 2 | — | Ethanol | 2 | MCT | Oily | 2.8 | 58.9 | 2.1 |

TABLE 3

| | Washing | Extraction | | | Concentration ratio of extract | | Astaxanthin content weight % | Crystal form | Dr. Carr's index |
|---|---|---|---|---|---|---|---|---|---|
| | Organic solvent (A) | Organic solvent (B) | Number of extraction stages | Powdering method | | Appearance | | | |
| Example 9 | Ethanol | Ethanol | 2 | Evaporation crystallization | 100 | Powder | 51.4 | Form I | 81 |
| Example 10 | Ethanol | Ethanol | 2 | Evaporation crystallization | 150 | Powder | 45.1 | Form I | 76 |
| Example 11 | Ethanol | Ethanol | 2 | Evaporation crystallization + Cooling crystallization | 50 | Powder | 30.7 | Form I | 64 |
| Example 12 | Acetone | Ethanol | 2 | Evaporation crystallization | 150 | Powder | 48.6 | Form I | 80 |
| Example 13 | Methanol | 2-Propanol | 2 | Evaporation crystallization + Cooling crystallization | 50 | Powder | 28.8 | Form I | 64 |
| Comparative Example 3 | — | Ethanol | 1 | Evaporation crystallization | 100 | The concentrate could not be filtered, and no powder was obtained. | | | |
| Comparative Example 4 | — | Acetone | 2 | Washing concentrate with deionized water and hexane | 13 | Powder | 50.7 | Form II | 53 |

Example 14, Comparative Example 5, Reference Example 1

Preparation of Composition for Administration

Safflower oil was mixed with each of the oily materials obtained in Example 1 and Comparative Example 1, and a commercially available astaxanthin composition (derived from *Haematococcus*) for reference to prepare a composition with an astaxanthin concentration of 0.5% by weight. These compositions were referred to as the compositions of Example 14, Comparative Example 5, and Reference Example 1, respectively.

<Evaluation for Absorption Rate on Mice>

The absorption rates of the compositions when orally administered to mice were compared by the following method. Each composition was orally administered to seven-week-old male ICR mice (available from CHARLES RIVER LABORATORIES JAPAN, INC.) at a dose of 50 mg of astaxanthin per kg body weight. The liver was collected from the mice at 2, 4, and 6 hours from the administration of the test substance. The collected liver was finely minced with scissors and weighed 0.3 g. Then, 2 mL of distilled water was added thereto and the mixture was homogenized with a Polytron homogenizer. Thereto was added 2 mL of methanol (containing 500 ppm of BHT), and the mixture was stirred for 10 seconds to deproteinize it. Next, 4 mL of n-hexane was added and the mixture was mixed for 5 minutes with a shaker. The resulting mixture was centrifuged (3000 rpm×10 min), and then the astaxanthin in the hexane layer was assayed by HPLC to calculate the astaxanthin concentration in the liver.

<Assay of Astaxanthin by HPLC>

The astaxanthin was assayed in the following analysis system. The retention time of astaxanthin was 9.1 min as determined in the following analysis system. As standard astaxanthin, a reagent from SIGMA CORPORATION was used.

Column: SYMMETRY C18 250 mm×φ4.6 mm (product of Waters)

Mobile phase: acetonitrile/ethyl acetate/water/formic acid=600/300/60/40 (volume ratio)

Detection wavelength: 471 nm

Flow rate: 0.8 mL/min

Figure 1:
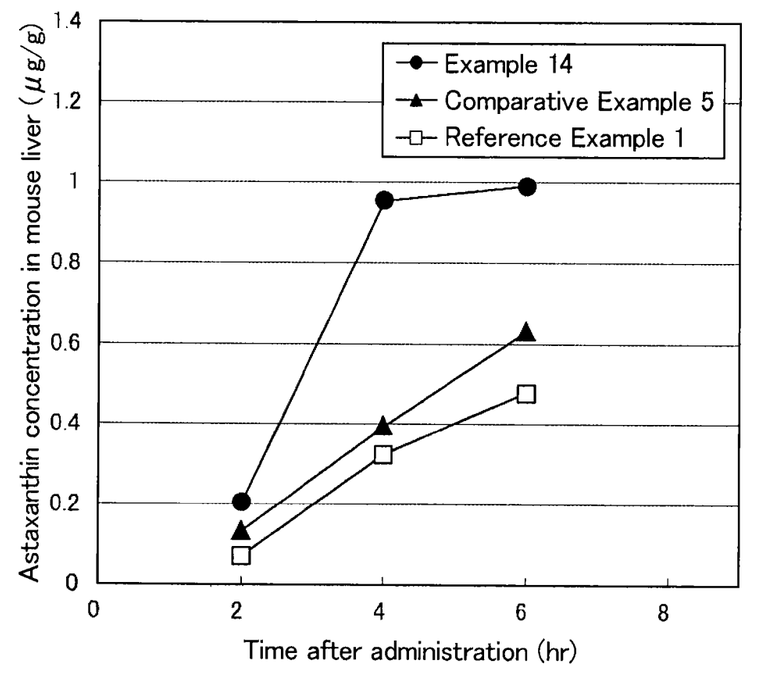
FIG. 1 shows the results of the absorption rates of the compositions of Example 14, Comparative Example 5, and Reference Example 1.

FIG. 1 shows the results. The composition (Example 14) containing the oily material of Example 1 was found to be ingested to provide a high concentration of astaxanthin in the liver and thus exhibit a high absorption rate in vivo, as compared with the composition (Comparative Example 5) containing the oily material of Comparative Example 1, which was prepared according to a conventional method.

The invention claimed is:

1. A method for producing a carotenoid composition, comprising:
   washing a carotenoid-containing yeast of the genus *Xanthophyllomyces* with a first organic solvent at 30° C. or lower to obtain a washed yeast; and extracting a carotenoid from the washed yeast with a second organic solvent at 10° C. to 70° C. to obtain a carotenoid extract.

2. The method according to claim 1, wherein the carotenoid is astaxanthin.

3. The method according to claim 1, wherein the first organic solvent is at least one selected from the group consisting of a ketone, an alcohol, a hydrocarbon, an ether, and a fatty acid ester.

4. The method according to claim 1, wherein the second organic solvent is at least one selected from the group consisting of an alcohol, a hydrocarbon, and an ether.

5. The method according to claim 1, wherein the first organic solvent and the second organic solvent are both ethanol.

6. The method according to claim 1, further comprising:
concentrating the carotenoid extract to form an oily composition.

7. The method according to claim 6, wherein the oily composition has an astaxanthin content of 1 to 20% by weight.

8. The method according to claim 1, further comprising:
precipitating a carotenoid from the carotenoid extract to obtain a precipitate; and
subjecting the precipitate to solid-liquid separation to form a powdered composition.

9. The method according to claim 8, wherein the powdered composition has an astaxanthin content of 20 to 80% by weight.

10. The method according to claim 2, wherein the first organic solvent is at least one selected from the group consisting of a ketone, an alcohol, a hydrocarbon, an ether, and a fatty acid ester.

11. The method according to claim 3, wherein the second organic solvent is at least one selected from the group consisting of an alcohol, a hydrocarbon, and an ether.

12. The method according to claim 2, further comprising:
concentrating the carotenoid extract to form an oily composition.

13. The method according to claim 3, further comprising:
concentrating the carotenoid extract to form an oily composition.

14. The method according to claim 2, further comprising:
precipitating a carotenoid from the carotenoid extract to obtain a precipitate; and
subjecting the precipitate to solid-liquid separation to form a powdered composition.

15. The method according to claim 3, further comprising:
precipitating a carotenoid from the carotenoid extract to obtain a precipitate; and
subjecting the precipitate to solid-liquid separation to form a powdered composition.

* * * * *